United States Patent [19]

Hay

[11] 4,059,657

[45] Nov. 22, 1977

[54] CALIBRATED ANESTHETIC VAPORIZER

[75] Inventor: Wayne W. Hay, Madison, Wis.

[73] Assignee: Airco, Inc., New Providence, N.J.

[21] Appl. No.: 595,186

[22] Filed: July 11, 1975

[51] Int. Cl.$^2$ .................... A61M 15/00; A61M 17/00
[52] U.S. Cl. ............................... 261/104; 261/39 R;
    261/DIG. 65; 128/188; 128/192
[58] Field of Search ................ 261/104, DIG. 65, 46,
    261/142, 39 R, 39 A; 128/186–188, 192–194,
    211, 212; 137/625.15, 625.46; 251/297

[56] References Cited

U.S. PATENT DOCUMENTS

| 1,333,048 | 3/1920 | Webster | 251/297 |
|---|---|---|---|
| 2,085,155 | 6/1937 | Heidbrink | 128/186 |
| 2,349,676 | 5/1944 | Pratt | 261/121 B |
| 2,553,446 | 5/1951 | Edmondson et al. | 128/188 |
| 2,968,474 | 1/1961 | Eichelman et al. | 261/DIG. 65 |
| 3,043,573 | 7/1962 | Chandler | 261/104 |
| 3,353,535 | 11/1967 | Gardner | 261/46 |
| 3,420,232 | 1/1969 | Bickford | 128/188 |
| 3,575,168 | 4/1971 | Jones et al. | 128/188 |
| 3,671,024 | 6/1972 | Breiling | 128/188 |
| 3,837,360 | 9/1974 | Bubula | 137/625.46 |
| 3,841,560 | 10/1974 | Sielaff | 239/136 |

FOREIGN PATENT DOCUMENTS

| 54,100 | 1/1938 | Denmark | 261/104 |
|---|---|---|---|
| 808,577 | 2/1959 | United Kingdom | 251/297 |

Primary Examiner—Tim R. Miles
Assistant Examiner—Gregory N. Clements
Attorney, Agent, or Firm—Roger M. Rathbun; Edmund W. Bopp; H. Hume Mathews

[57] ABSTRACT

Anesthetic vaporizer of the flow-through type having a calibrated flow control valve unit for proportional distribution of the inlet gas between a vaporizing chamber and a main bypass passage to obtain a desired anesthetic concentration. A rotary, multiple-port valve with a multiplicity of laminar flow-type passages in parallel is operable in discrete steps for adding the anesthetic vapor from the chamber in predictable increments to a preset flow of the inlet gas for proportional gas division. An auxiliary gas bypass for temperature compensation has a cone-type valve with restricted opening controlled by a temperature responsive motor in the vaporizing chamber. A wick assembly in the anesthetic vaporizing chamber guides the chamber gas through a multiplicity of parallel passages formed by stacked sheets of absorbent and corrugated materials respectively, to obtain maximum vaporization of the anesthetic.

12 Claims, 11 Drawing Figures

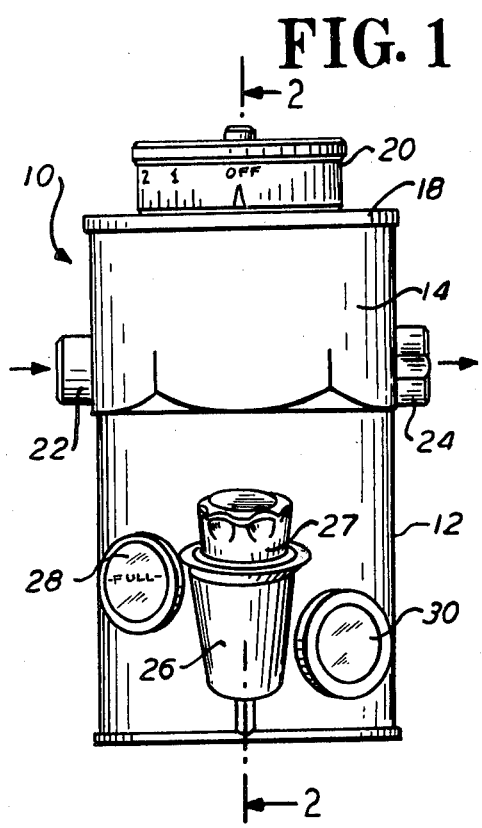
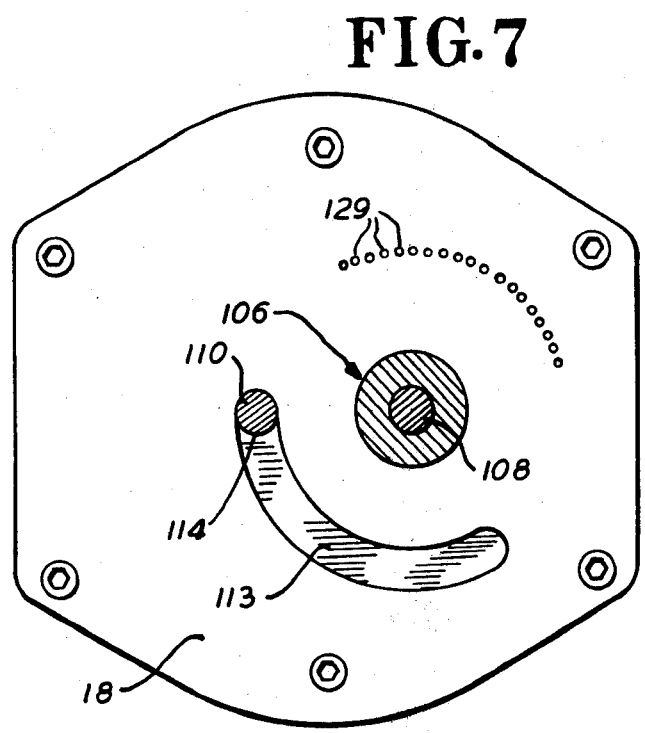
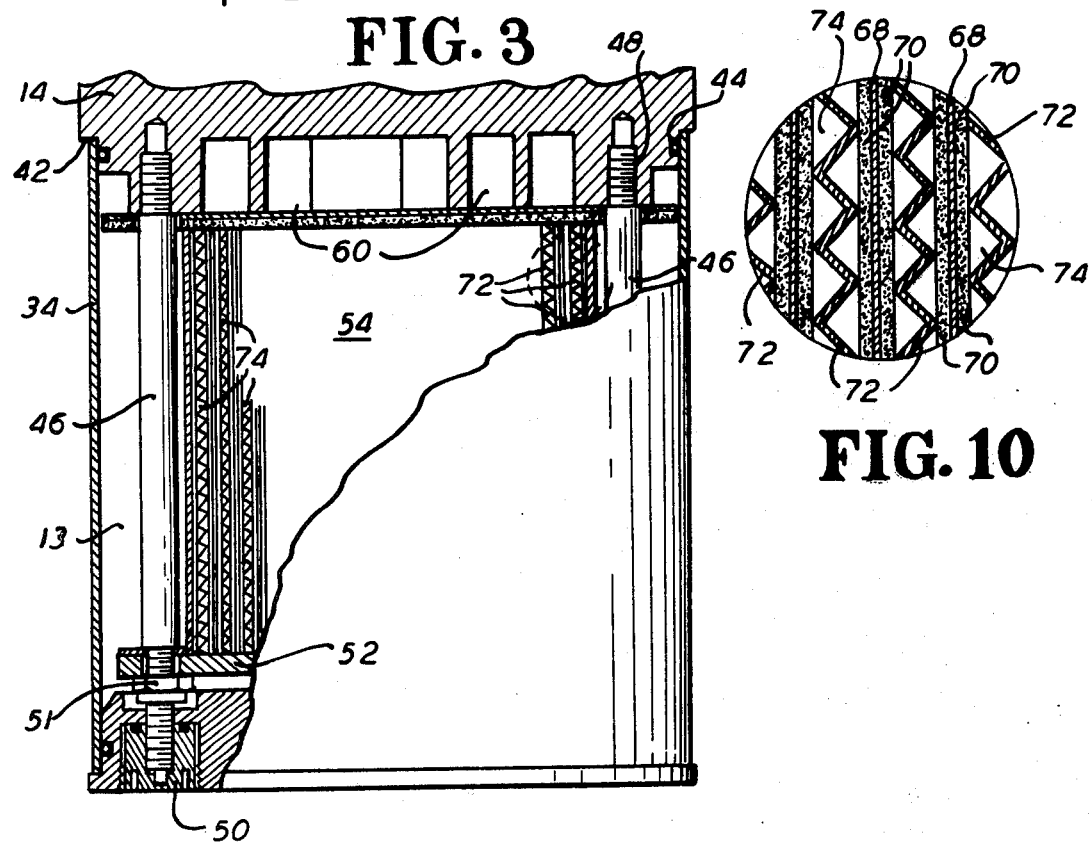

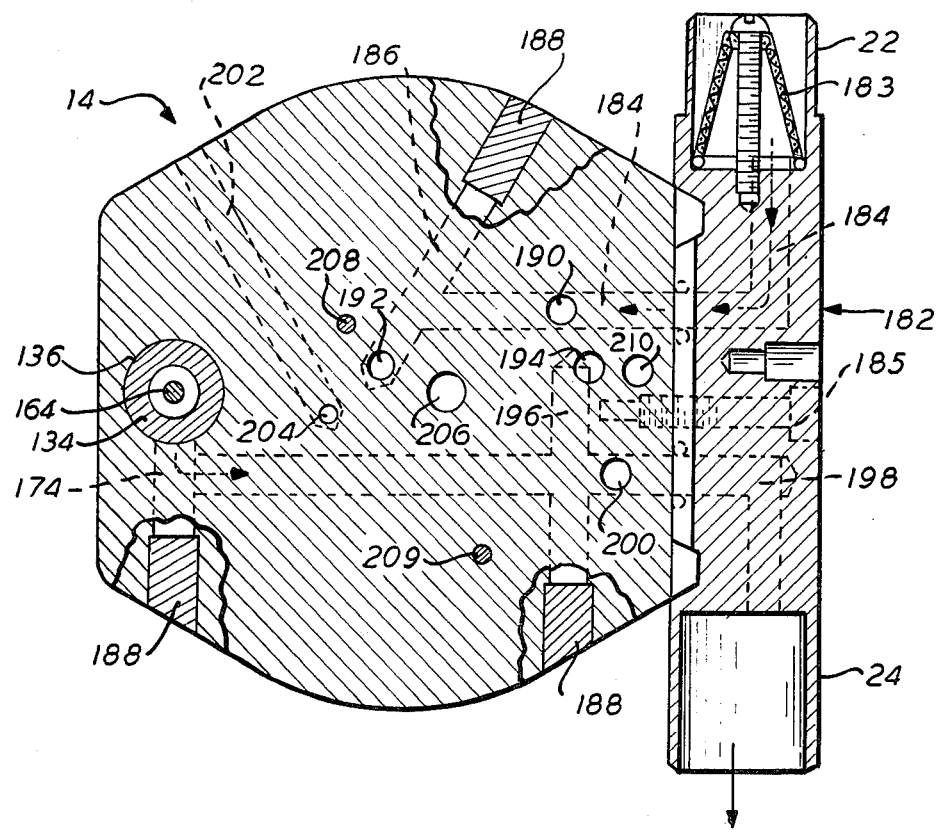
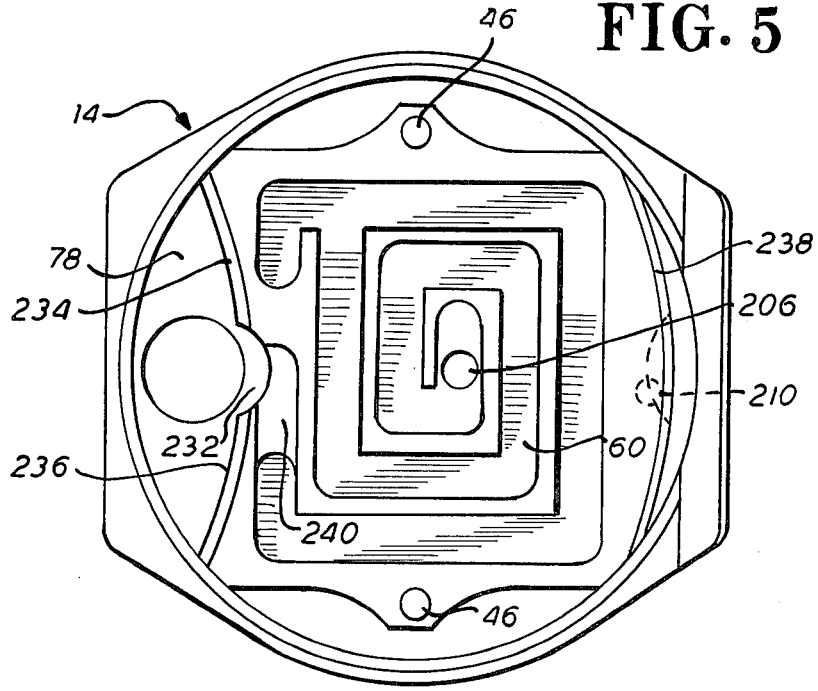

FIG. 8
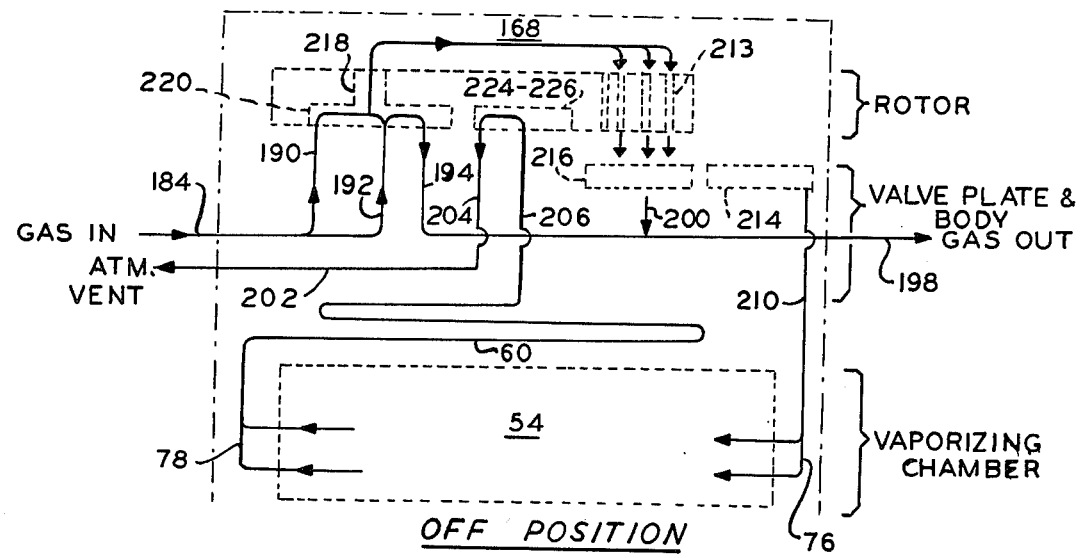
*OFF POSITION*
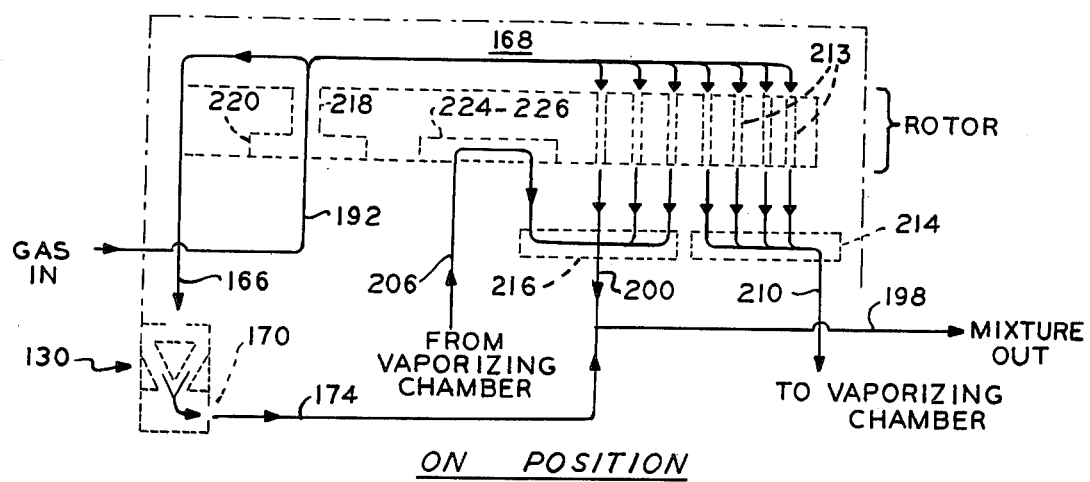
*ON POSITION*
FIG. 9

CALIBRATED ANESTHETIC VAPORIZER

BACKGROUND OF INVENTION

Anesthetic vaporizers have been proposed wherein the gas (or air) inflow to the vaporizer unit is proportionately divided between a path through the vaporizing chamber containing the anesthetic liquid, and a path bypassing the chamber so that the mixture at the vaporizer outlet represents a desired concentration of the anesthetic according to patient requirement. Since operation of the vaporizer results in heat extraction from the chamber, a temperature compensating valve, generally in the outlet passage of the chamber, is usually provided to increase proportionate flow through the chamber as the vaporization rate decreases with decrease in chamber temperature.

The prior art devices for the most part have not been entirely satisfactory in overcoming certain technical problems, such as maintaining the selected concentration of anesthetic substantially constant irrespective of changes in the flow rate of the gas and/or the temperature of the vaporizer chamber within preselected ranges of gas flow and chamber temperature. Another problem is involved in the operation of multiple controls for making full use of the vaporizer, that in turn generally results in a more complex and costly structural design.

A vaporizer unit constituting an improvement over prior art devices in precision control of the selected anesthetic concentration, is disclosed in U.S. Pat. No. 3,841,560 granted Oct. 15, 1974 to Ulrich Sielaff and assigned to the same assignee as the present invention. The present invention is an improvement thereon, especially as to incorporation of all manual control functions in a single rotary valve assembly, a simplified temperature compensation bypass, and other features that are described herein.

SUMMARY OF INVENTION

The anesthetic vaporizer of this invention comprises a compact, integrated unit including essentially a vaporizing chamber containing liquid anesthetic, a calibrated flow control valve assembly for dividing and proportioning the flow of incoming gas between separate paths in laminar flow to the vaporizing chamber and to a bypass respectively, so that there is a desired anesthetic concentration in the vaporizer outlet mixture, and an auxiliary bypass with a variable restricted passage for providing temperature compensation of the mixture according to variation in the vaporizing chamber temperature. The restriction is formed by a cone-type valve having a predetermined minimum opening and operable by a temperature response device in the chamber.

Calibrated proportional flow control is achieved by a multiple-port rotary valve of the shear-type wherein the rotary element is manually positioned by a single calibrated knob, and has a multiplicity of parallel, capillary-type openings for determining the proportioning and division of the gas flow as described aove; in addition, the rotary valve is arranged to shut off the vaporizing function without interfering with normal flow of gas through the vaporizer to the patient, and in its "off" position to vent the vaporizing chamber to atmosphere.

A further feature of practical importance is an improved wick assembly in the vaporizing chamber wherein the incoming gas is directed through a multiplicity of parallel, horizontal passages formed by stacked sheets of anesthetic absorbent material, corrugated material and heat conducting metal such as copper, respectively. The resulting large vaporization area of the absorbent material forming walls of the multiple passages, combined with the heat inflow conducting function of the copper sheets, provide maximum vaporization capacity for the liquid anesthetic.

A principal object of the invention therefore is an improved calibrated anesthetic vaporizer of the flow-through type that by a single dial setting of a multiple-port rotary valve, is capable of adding to a preset flow of gas the vapor of a volatile liquid anesthetic in predictable increments over a range from zero to a selected maximum concentration.

Another object is an improved vaporizer of the character above, that is capable of maintaining the selected concentration substantially constant irrespective of changes in the flow rate of gas and/or the temperature of the vaporizing chamber within pre-selected ranges of gas flow and chamber temperature, respectively.

A further object is an improved vaporizer of the character above, wherein the gas flow through an auxiliary bypass having a cone-in-cone type valve is variably controlled within limits of laminar flow, according to the temperature of the vaporizing chamber for maintaining the selected concentration.

A further object is an improved wick assembly for the vaporizing chamber wherein the gas flow through the chamber is divided into a multiplicity of small transverse passages in the assembly, the walls of which are formed in part by anesthetic absorbing material for obtaining maximum vaporization of the anesthetic.

Other objects, features and advantages will appear from the following description with reference to the accompanying drawings.

BRIEF DESCRIPTION OF DRAWINGS

FIG. 1 is a view in elevation of the anesthetic vaporizer unit;

FIG. 3 is a partial sectional view of the vaporizer, taken along the line 3—3 of FIG. 2, illustrating the vaporizing chamber wick assembly and detail thereof;

FIG. 4 is a view in transverse cross-section of the vaporizer body taken along the line 4—4 of FIG. 2;

FIG. 5 is a transverse sectional view of the vaporizer taken along the line 5—5 of FIG. 2 from beneath the vaporizer body;

FIG. 7 is a top view of the vaporizer cap taken along the line 7—7 of FIG. 2;

FIG. 8 is a schematic illustration of vaporizer passages controlled by the rotary valve in the "OFF" position;

FIG. 9 is a similar illustration of a valve operating position wherein gas flow is proportional between the vaporizing chamber and main bypass, and FIG. 10 is an enlarged detail view of the vaporizer chamber wick assembly.

DESCRIPTION OF PREFERRED EMBODIMENT

Figure 2:
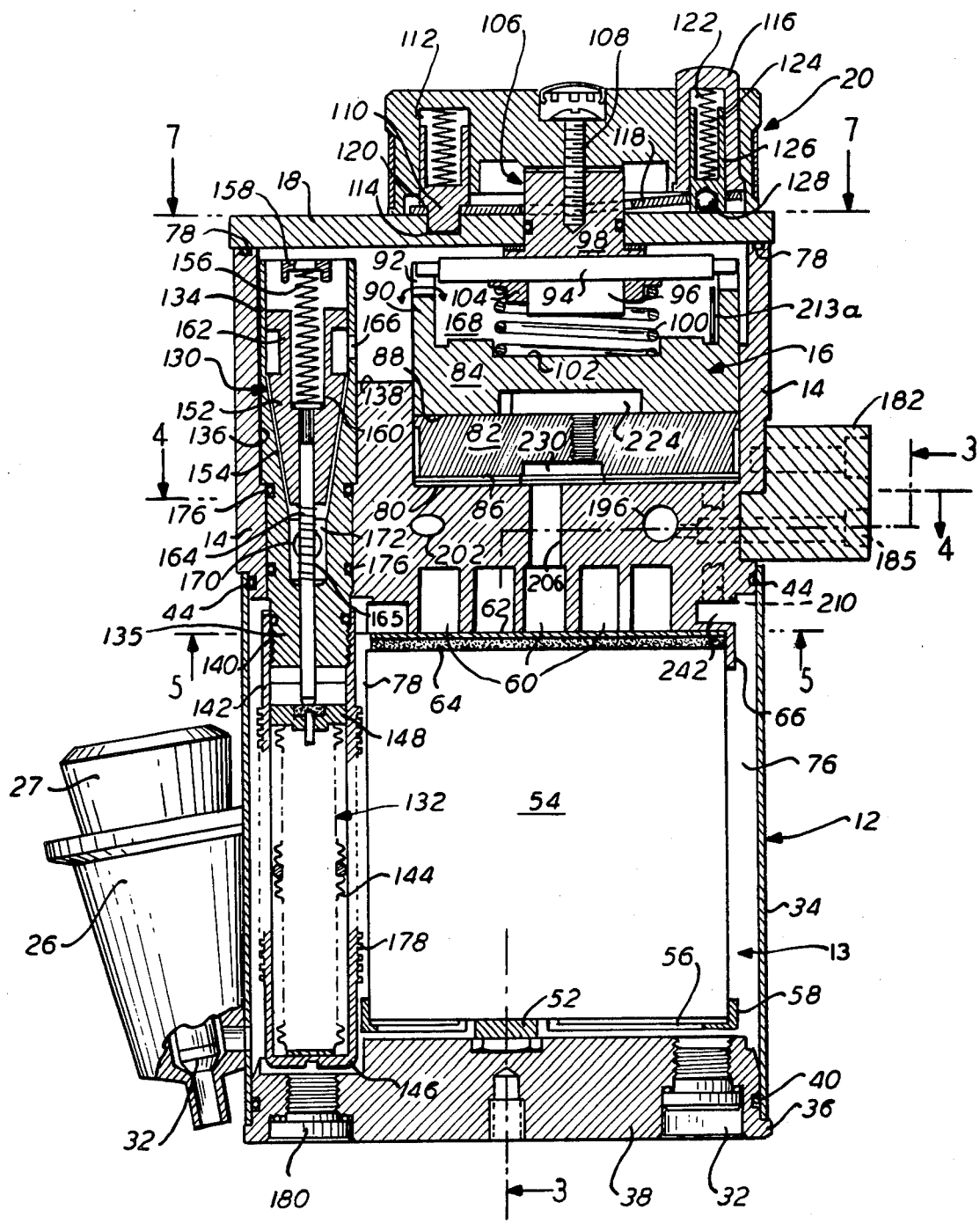
FIG. 2 is an enlarged elevational view of the vaporizer unit, generally along the sectional line 2—2 of FIG. 1.

Referring to FIGS. 1 and 2, the anesthetic vaporizer constitutes an integrated structural unit 10 that is compact and readily portable. The unit comprises essentially a base housing 12 for the vaporizing chamber 13, a valve body 14 mounted on the housing for enclosing and seating a unitary rotary valve 16, FIG. 2, that controls most venting and gas flow through the vaporizer, a cover cap 18 for the valve body and a calibrated knob 20 seated on the cap for operating the valve. The valve ody is connected through a manifold to gas inlet and outlet couplings 22 and 24 that in practice are connected respectively, to a suitable gas (or air) source, and to an exhaust line for the recipient of the anesthetic-gas mixture. The base housing 12 which contains a liquid anesthetic, is provided with the usual fill-funnel 26 and cap 27, visual maximum and minimum liquid level indicators 28 and 30 respectively, and suitable drain means at the bottom of the housing, such as drain plug 32.

Referring specifically to FIG. 2, the base housing 12 and valve body 14 which are substantially aligned, are roughly of cylindrical form as indicated in section, FIG. 4. The housing comprises an outer shell 34 that seats at its lower edge on an annular shoulder 36 of a supporting base plate 38. A sealing O-ring 40 provides a fluid-tight joint between the shell and base. The valve body 14 has a recessed shoulder 42, FIG. 3, that seats on the upper edge of the shell wall 34. A fluid seal between the overlapping surfaces of the body and shell is made by O-ring 44. For securing the shell between the base 38 and valve body 14, tie bolts 46, FIG. 3, have their upper ends anchored in the valve body as shown at 48, and their lower ends connected to sealing nuts 50 in the base plate for tensioning the tie rods.

The tie bolts 46, together with securing means including nuts 51, also support and position a transverse bar 52 that serves as a support and clamp for a wick assembly 54 constituting a generally rectangular stack of laminations substantially filling the vaporizing chamber 13. For supporting the lower corner edges of the stack, a frame 56 with edge-positioning flanges 58 is mounted on the transverse bar 52.

Referring now to the valve body 14, FIG. 2, the lower side thereof extending into the shell 34 has formed therein a labyrinth-like passage 60, FIGS. 2, 3 and 5, open at its lower side. This side is covered by a thin resilient plate 62 and that is biased through a sheet of compressible material 64 against the vaporizer body by the wick stack 54 and clamping bar 52. Depending peripheral flanges 66 on the valve body serve to hold in position the upper part of the stack.

The wick assembly, referring specifically to FIGS. 3 and 10, is made up of a series of stacked laminations of different materials, the plane of each extending substantially the distance between the depending flanges 66, FIG. 2. The laminations are preferably of three types, the first referring to the enlarged detail view, FIG. 10, being a thin sheet 68 of heat conducting metal such as copper, constituting the first, fifth, ninth, etc. and last lamination. The second type is a sheet 70 composed of material having the absorbent properties of a wick, such as blotting paper, constituting the second, fourth and all even-numbered laminations, and the third type is a sheet 72 having corrugations whose elements lie in horizontal planes, constituting the third, seventh, eleventh, etc. lamination. It is therefore seen that each copper sheet makes with two absorbent sheets a laminated unit that is in turn, between two corrugated sheets. The spaces between the corrugations of each sheet and the adjacent absorbent sheets at opposite sides form a multiplicity of horizontal passages 74, one wall of which is saturated with the liquid anesthetic. The top edges of the laminations are biased against the compressible sheet 64 by the clamping means described above. The first and last copper sheets of the stack are sealed by their vertical (lateral) edges against the side walls of the shell due to the stress imposed by tightly packing the laminations in the chamber. The intermediate sheets of the stack are spaced at their lateral edges from the side walls of the shell to form vertical passages 76 and 78, FIG. 2, that communicate respectively, with opposite ends of the multiple passages 74. Hence, it will be seen that gas flowing laterally through the stack in a large number of separate parallel paths is in contact with large surface areas of the absorption material that in turn is in planar contact with the heat conducting copper sheets. Thus, the heat inflow from the outer wall regions of the vaporizer through the copper sheets together with the liquid in the vaporizing chamber 13, tend to stabilize the wick stack temperature in opposition to the cooling effect of vaporization. Accordingly, a constant high rate of vaporization of the anesthetic liquid is achieved within the vaporizing chamber.

Figure 6:
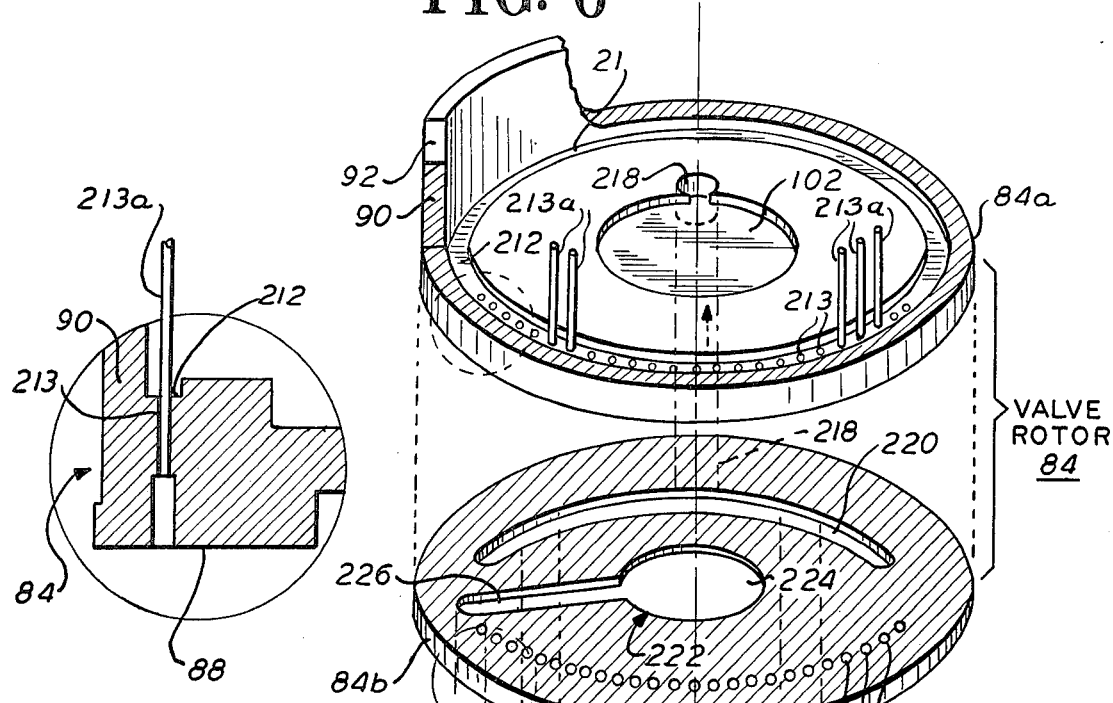
FIG. 6 represents the rotary control valve assembly and related gas passages of the vaporizer body in an exploded view.

Returning again to FIG. 2, the valve body at its upper end is formed as a cylindrical shell on which the vaporizer cover cap 18 is suitably mounted and sealed by O-ring 78. The body preferably is an aluminum extrusion and has formed in the main lower portion thereof passages connecting with the vaporizer inlet and outlet couplings 22 and 24, that together with the rotary valve 16 define the main vaporizer bypass, the gas distribution passages to the vaporizing chamber, and vents, etc. for non-operating conditions. The valve body on its upper side has a circular land 80 that forms a base for the rotary valve assembly, the assembly in turn comprising a disc-like brass plate 82 that constitutes a valve seat for the valve rotor 84, also of brass. The valve seat plate and valve body have aligned ports for respective gas passages as indicated in FIG. 6 and described below, and are held in fixed relative position by dowel pins. A correspondingly apertured sealing gasket 86 is positioned between the valve seat plate and body.

The valve rotor 84 comprises a circular seating portion 88 that is spring-biased against and makes rotary sliding contact with the valve seat plate 82. The rotor has a vertical peripheral flange 90 extending from the seating portion 88 and having at its upper edge diametrically positioned slots 92. A coupling pin 94 rides in the slots and fits at its mid-section within a slot 96 in the lower end of the rotor operating stem 98. The stem is rotatably mounted in the vaporizer cover cap 18 and sealed thereto by an O-ring, as indicated. The rotor biasing spring 100 seats at its lower end within a circular recess 102 in the rotor, and at its upper end against a washer 104 centered on the stem and bearing against the pin 94. The stem has at its upper end a tongue-and-slot connection 106 with the control knob or dial 20 and is secured thereto by a screw 108. Accordingly, rotation of the calibrated dial positions the valve rotor in corresponding steps.

For ensuring against accidental release of the dial in its "off" position, a locking detent 110 is positioned in a recess 112 in the dial knob where it is spring-biased toward the cover cap 18 and into a shallow arcuate slot 113 therein, FIG. 7. This slot has at its terminal or "off"

position, a hole 114 into which the detent can be biased, thereby locking the knob. For restricting to positive action the release of the knob from the off position, a release button 116 extends through and above the knob for actuating a detent release lever 118. The lever is apertured to engage a shoulder 120 on the detent so that depression of the button rotates the lever clockwise to lift and release the detent.

The release button, in addition, has a central recess 122 for a biasing spring 124 that bears at its upper end against the button and at its lower end against a sleeve-like detent 126 that in turn extends through a hole in the lever 118. The button is thereby biased toward its upper position, and the detent toward the vaporizer cap. A stell ball bearing 128 in the lower end of the detent makes engagement with shallow pockets 129 closely spaced in an arcuate path on the vaporizer cap, FIG. 7, thereby to provide dial (and valve) adjustment by discrete or incremental steps.

The vaporizer auxiliary bypass referred to above, FIG. 2, has a temperature compensating valve 130 and a thermal motor or temperature sensing actuator 132, that are mounted in alignment within a vertical space at one side of the vaporizer unit. The valve is mounted in a cylindrical housing 134 that is positioned within a bore 136 extending through a second land 138 of the valve body, and has an adjustable screw threaded connection at 140 with a depending cylindrical housing 142 in which the thermal motor 132 is mounted. The thermal motor comprises a metal bellows 144 of known type, that is seated at its lower end on the cylinder end wall 146. Its upper end is formed as a disc 148 that is slidable within the cylinder with expansion or contraction of the bellows. The disc is operatively connected with the valve 130 through the valve stem 164. Suitable limit-stop or spacing means, such as a wire 165 wound around the valve stem between the valve and the valve housing, serves to block valve closing beyond a certain clearance. As will presently appear, this defines a predetermined minimum restricted opening for the auxiliary bypass valve 130, notwithstanding possible further contraction of the bellows 144.

The bypass valve is of the cone-in-cone type and comprises a vertically moveable conical member 152 that has a corresponding conical seat 154 formed in the valve housing. The valve cone at its base is biased towards its seat by a spring 156 seated within a bracket 158 at the upper end of the valve housing, and within a recess 160 in the cone. The cone base also has a guide extension 162 for both the spring and valve. The valve stem 164 depends from the cone apex, through the lower part 135 of the valve housing and into abutting engagement with the bellows disc 148; accordingly, the position of the bellows disc (except for the contraction limit, above) determines the extent of valve opening. As this opening is never less than a predetermined minimum and is always comparatively restricted in cross-section in relation to its length, the gas flow therethrough is characteristic of laminar flow. It will therefore be seen that the minimum valve clearance represents a fixed laminar flow bypass, and increasing the clearance corresponds to a variable laminar flow bypass.

The valve housing at its upper end has an inlet port 166 that connects with the space 168 above the valve rotor, and an outlet port 170 leading from a chamber 172 below the valve. This chamber connects with an exhaust passage 174 in the main valve body, FIG. 4, leading to the vaporizer outlet 24. Since, as will presently appear, the space 168 above the valve rotor is connected to the inlet gas port of the vaporizer, the bypass valve 130 controls a passage that completely bypasses the vaporizing chamber. Sealing O-rings 176 prevent gas leakage from the gas space 168 to the vaporizing chamber below.

The cylindrical bellows housing 142 is positioned in the chamber outlet passage 78 closely adjacent to the exhaust side of the wick stack transverse passages 74 so as to be readily responsive to change in temperature of the stack exhaust gases. For improved thermal response, the cylinder 142 is provided with peripheral fins 178 as shown, for increasing the heat transfer surface. The bellows within the housing accordingly tends to expand or contract with housing temperature change, thereby positioning the bellows disc 149 accordingly and adjusting the valve stem and cone valve to vary the valve opening. For adjusting the vertical position of the bellows housing itself with respect to the lower end of the valve stem and hence setting as desired the initial valve response, a plug 180 in the base plate 38 is removed and a screwdriver inserted to rotate the slotted housing end wall 146. This raises or lowers the bellows housing (through the screw thread connection 140) with respect to the upper valve housing 134.

The gas passages in the valve body referred to above, are best shown by FIGS. 4 and 5, taken with FIGS. 2 and 6. Referring first to FIG. 4, the gas inlet and outlet couplings 22 and 24 form part of a manifold 182 that is suitably secured by bolts 185 to the valve body 14. The inlet coupling 22 connects through a filter 183 with the main gas inlet passage 184 that in turn leads into a lateral passage 186. This passage, as are the others, is formed as a bore in the valve body, and where indicated is sealed by a plug 188 at the bore entrance.

The horizontal body passages 184 and 186 are intersected by parallel vertical passages 190 and 192 respectively, that show as corresponding openings in the top face of the valve body 14, FIG. 6. The vaporizer body hs a vertical exhaust bore 194, FIGS. 4 and 6, that intersects the lower transverse bore 196, that in turn connects with the manifold outlets or exhaust passage 198. Also intersecting the outlet passage 198 is a parallel vertical exhaust passage 200, the upper body opening thereof showing in FIG. 6. The valve body also has a transverse venting passage 202 that opens to atmosphere, and leads from a vertical intersecting passage 204, FIG. 6.

An off-center vertical bore 206 extends through the valve body for connecting the lower labyrinthean passage 60, FIG. 5, leading from the vaporizing chamber with the rotary valve seat port 228, FIG. 6. A vertical bore 210 extends through the valve body for connecting the vaporizing chamber inlet passage 76 leading into the wick chamber, FIG. 2, with an upper valve seat port 211, FIGS. 2 and 6.

For preventing any rotation of the valve plate 82 with respect to the valve body 14, a pair of dowel-pins 208 and 209 (shown in section) extend as indicated through aligned bores in the plate and body, respectively.

Figure 11:
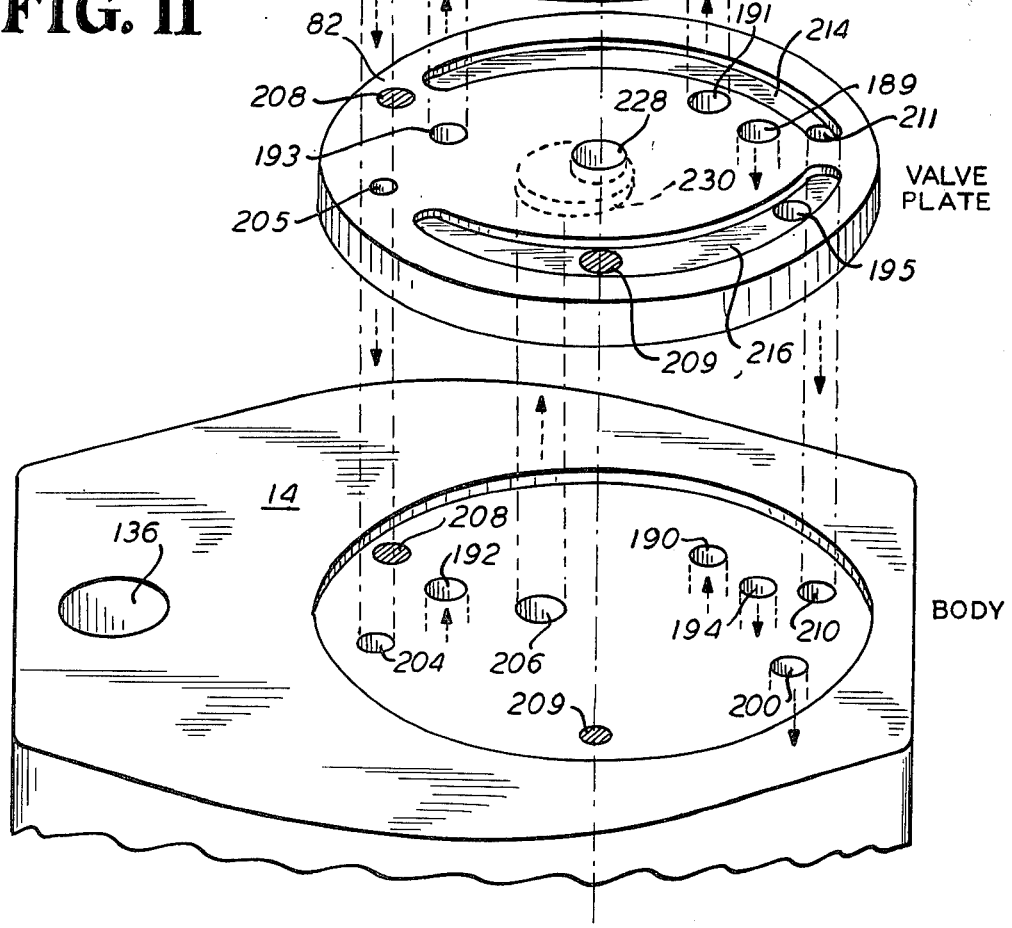
FIG. 11 is an enlarged detail view of the small diameter bores and tubes which achieve the laminar flow effect.

Referring more specifically to the partly schematic illustration of FIGS. 6 and 11 the valve rotor 84 is shown as transversely split into upper and lower sections 84a and 84b for better illustrating the relation of the passages, etc. in the upper and lower parts thereof. The upper side 84a (with the peripheral flange 90) has a circular groove 212 wherein a multiplicity of small diameter bores 213 having laminar type flow characteristics are closely spaced along an arc of somewhat less than 180°. As illustrated in FIG. 11, the bores which extend through the rotor, have stepped diameters and are of restricted diameter throughout their length in relation to their length. For enhancing laminar flow effect, open-end tubes 213a are inserted as illustrated in the upper openings respectively, of the corresponding bores 213 along the groove 212. Although the laminar flow type passages defined by the bores and tubes respectively, are illustrated for simplicity as having generally similar diameters for uniform linear-type flow, it is preferred in accordance with the invention that the increments of anesthetic concentration be non-uniform rather than have a linear function. For example, the passages may be grouped accordind to diameters to have 12 increments of 0.125% each, anesthetic concentration by volume, six increments of 0.25% each and four or more increments of 0.5% each, all in accordance with dial marking. However, it is within the spirit of the invention that the increments be uniform for linear-type flow throughout the complete scale if so desired.

The rotor bores 213 are in whole or partial alignment, according to the angular position of the rotor, with corresponding arcuate slots 214 and 216 on the upper side of the valve plate 82. The arcuate slot 214 also connects with the vaporizing chamber through the port 211 and vertical bory bore 210, and the arcuate slot 216 connects with the main exhaust passage through port 195, etc., as described above.

A hole 218 extends through the upper rotor section 84a and into the arcuate slot 220 in the lower side of the rotor section 84b. The hole (port) 218 also opens into the vaporizer upper body space 168, FIG. 2, above the valve rotor. There is also formed in the lower rotor section 84b, a keyhole shaped slot 222 comprising an enlarged circular central portion 224 and a laterally extending narrow slot 226, the end of which is in substantial alignment with the arc defined by the rotor bores 213.

Referring briefly to the fixed valve body and doweled valve seat plate, the plate at its upper side has a central bore 228 in alignment with the rotor slot portion 224 above. At its lower end, the bore merges into a larger diameter counterbore 230 that is somewhat off-center in order to connect with the lower offset body bore 206. Likewise, the valve plate has a port 205 that is positioned in the arc traversed by the outer end of the key slot 226. The port 205 is in alignment with the lower body bore 204 that vents to atmosphere.

FIG. 5 shows the ports and passages on the under side of the valve body for leading the anesthetic mixture upward from the chamber mixture passage 78, into and through the valve body to the valve seat plate. The boundaries of the labyrinth 60 are defined in part by arcuate flanges 234, 236 and 238. The space 232 between the flanges 234 and 236 defines a passage interconnecting the lower chamber outlet passage 78 and the entrance 240 to the labyrinth that leads to the central vertical bore 206, which in turn, FIG. 6, leads as described above to the rotary valve. The vaporizing chamber inlet passage comprises the vertical bore 210 leading from the valve plate as mentioned above, and terminating in a lateral recess 242 in the valve body, FIG. 2. This recess communicates with the vertical chamber passage 76 directly beneath, that in turn connects with the entrance openings of the multiple wick passages 74. This completes a path from the gas inlet coupling, through the rotary valve and vaporizing chamber, to the mixture outlet coupling.

OPERATION OF VAPORIZER

In the "OFF" position of the vaporizer represented approximately by the relative positions of the valve assembly in FIG. 6 and schematically in FIG. 8, the vaporizing chamber 13 is vented to atmosphere, and the gas inlet path is expanded in effect by parallel flow for ensuring a low resistance flow path directly through the vaporizer to the outlet or exhaust opening 198, FIG. 4. As generally described above, the vaporizing chamber venting path is by way of the chamber vertical outlet passage 78, labyrinth 60 and the body and plate openings 206 and 228 that lead into the rotor key slot 224–226. In this off position, the outer end of the key slot 226 is positioned directly above the venting bores 204–205 which leads to atmosphere through the lateral body passage 202.

The parallel flow-through paths above start at the main inlet passage 184 that feeds into two parallel vertical passages 190 and 192, both of which terminate in corresponding valve plate ports 191 and 193. In the off position, both ports, as well as the exhaust port 189, are in registry with the overhead rotor arcuate slot 220. From this slot, the joined streams of incoming gas flow in major part into the exhaust port 189, body bore 194, etc. (FIG. 4), for direct, low-resistance flow through the vaporizer. Minor flow would also occur upward through the slot port 218 (upper rotor section 84a) into the space 168 above the rotor where it would again divide into two paths that lead respectively into the auxiliary temperature controlled bypass described above, and in reverse laminar bypass flow through the rotor by way of the parallel connected restricted passages 213–213a. Due to the relatively higher flow resistance of these passages, the direct flow-through path (which includes exhaust port 189) carries in the off position of the vaporizer most of the gas therethrough.

Since in this off position, the capillary passages 213 are only in registry with the arc defined by the plate slot 216, that part of the gas flow will be through the slot outlet port 195, into the body bore 200 and out through the main exhaust passage 198. There can be no flow through the vaporizing chamber in the off position as the other plate slot port 211 in slot 214 leading to the vaporizing chamber inlet bore 210 is sealed off by the rotor. In this position, the rotor valve under-face completely covers the slot 214 which is on a larger radius arc than that of the rotor slot 220 overhead.

Assuming now that the vaporizer is turned on by depression of the "release" button 116, FIG. 2, and subsequent rotation of the dial 20 and rotor in the counterclockwise direction, say about 20° as viewed in FIG. 6, the key slot 226 will be moved out of registry with the chamber venting port 205, and into registry with the adjacent end of the valve seat plate slot 216, thereby connecting the chamber to exhaust path through the slot port 195 and bore 200 that intersects the main exhaust passage 198. The small-radius rotor slot 220 no longer connects with the plate exhaust port 189, FIG. 4, so that all gas flow is now forced through the rotor port 218 upward into the space 168 above the rotor, from which it reverses to flow through the auxiliary temperature compensating bypass and passages 213. In this position of initial opening, a few leading passages 213 are above the plate slot 214 and port 211, thereby establishing a limited flow path to the wick (vaporizing) chamber 13. The temperature compensating bypass as indicated in FIG. 9, is connected at all times across by vaporizing chamber between the vaporizer inlet and outlet passages 184 and 198, respectively.

Further rotation of the dial to about 60°, now brings more of the arc defined by the row of rotor passages 213 into registry with the opposite slot 214, the outlet port 211 of which leads as described to the vaporizing chamber inlet 76, FIG. 2 and 5.

As schematically shown in FIG. 9, the incoming gas from the space above the rotor now is in divided flow, i.e. the flow from the leading part of the arcuate row of passages 213 being downward into the plate slot 214, from where it goes into the vaporizing chamber by way of port 211, etc. The gas flow in the trailing row of passages 213 constitutes a minor bypass flow into the seat slot 216 and through port 195 and body bore 200 to exhaust at passage 198. The main bypass flow in this instance also is through the thermal bypass, including the valve 130.

The vaporizing chamber exhaust, which is saturated with anesthetic vapor as described above, flows upward from the labyrinth 60 into the rotor key slot 224-226, reversing into the aligned seat slot 216 beneath, and therefrom through port 195 and bore 200 to mix with the main bypass and auxiliary bypass gases in the exhaust passage 198. This mixture comprises the desired anesthetic concentration.

As the wick capillary action keeps the wick wet throughout its height, lowering of the level of the liquid anesthetic has no significant effect on the rate of vaporization within the wick passages 74. The anesthetic concentration accordingly is not affected by changes in the liquid level.

The exhaust gas from the wick passages is as indicated above, saturated with the anesthetic vapor and therefore reduced in temperature. As the temperature of the saturated gas is substantially uniform at the discharge end of the wick stack, the temperature of the adjacent bypass thermal motor tends to be at the same level. As increased temperature at the thermal motor results in its acial expansion, thereby opening the auxiliary bypass valve further and allowing a larger fraction of the total gas flow to bypass the vaporizing chamber, the increased concentration of vapor in the chamber exhaust gas due to increased temperature, is offset and vice versa.

Since the properties of all the passages 213 in the valve rotor 84 provide for laminar flow, the flow through the vaporizing chamber at any vaporizer temperature corresponds to those groups of passages delivering gas to the chamber; the calibration of the control knob dial may therefore be made linear, as the spacing between the passages 213 is assumed to be constant. Thus, it will be seen that by selective adjustment of the rotor dial 20, vaporized anesthetic can be added to a preset flow of gas through the rotor in predictable increments within a complete range up to a selected maximum concentration of the anesthetic.

When the valve rotor is turned to its fully "open" position, there is no flow through passages 213 into the plate slot 216 which includes the main bypass port 195. Hence, all flow is through the vaporizing chamber and wick stack and the auxiliary temperature compensating bypass valve 152. As regards the vaporizer flow resistance, the pressure drop through the wick stack is very small as compared with that through the rotor passages 213 and can be disregarded.

In summary, the improved calibrated anesthetic vaporizer of this invention is capable of adding to a preset flow of gas an anesthetic vapor in predictable increments over a wide range of anesthetic concentration, while maintaining the selected concentration substantially constant irrespective of changes in the flow rate of the gas or the vaporizing chamber temperature, or both, within predetermined ranges of gas flow and chamber temperature.

Having set forth the invention in what is considered to be the best embodiment thereof, it will be understood that changes may be made in the system and apparatus as above set forth without departing from the spirit of the invention or exceeding the scope thereof as defined in the following claims.

I claim:

1. An anesthetic vaporizer for adding the vapor of a volatile liquid anesthetic in predictable increments to a preset flow of gas comprising:
   a. a gas inlet passage and a gas and vapor outlet passage,
   b. a vaporizing chamber containing liquid anesthetic,
   c. a rotary valve assembly for controlling passages connecting the vaporizing chamber to the inlet and outlet passages, and for bypassing the vaporizing chamber comprising a disc-like valve rotor and an enclosing cylinder-like body having a fixed circular seat for the rotor,
   d. the rotor and seat being in planar contact and having in combination a plurality of ports and passageways arranged to form a first proportioning multiple-passage laminar-flow control path from the gas inlet passage through the vaporizing chamber to the outlet passage, and a second proportioning multiple-passage laminar-flow control path from the gas inlet passage through the valve bypassing the vaporizing chamber to the outlet passage,
   e. the valve rotor having a calibrated operating dial and being angularly adjustable to proportion the flow between the first and second paths for adjusting the vapor concentration in the outlet mixture,
   f. a third laminar-flow control path for connecting the gas inlet passage to the outlet passage to bypass the vaporizing chamber, said third path having a single variable restriction for laminar flow control that is defined by nested conical members with restricted spacing for preset minimum laminar flow,
   g. temperature responsive means in the vaporizing chamber for varying the spacing between the conical members to thereby control gas flow in said third path and compensate for variations in the vapor pressure of the liquid anesthetic, and
   h. the enclosing valve body defining an inlet gas chamber above the valve rotor and the valve rotor having an arcuate slot on its seating face that connects through a rotor port with the chamber, and with the gas inlet through the valve seat for admitting gas to the chamber, the rotor having diametrically opposite the arcuate slot spaced laminar flow type parallel passages defining an arc having a greater radius than the arcuate slot, the passages leading from the inlet gas chamber in divided flow to passageways in the valve seat that lead in turn respectively, to the vaporizing chamber and directly to the outlet passage to bypass the vaporizing chamber.

2. An anesthetic vaporizer as specified in claim 1 wherein the rotor arcuate slot in the valve off-position connects through a second seat port with a gas outlet passage for low resistance flow directly through the vaporizer.

3. An anesthetic vaporizer as specified in claim 1 wherein the valve body has a cover with an arcuate row of shallow pockets that are spaced in correspondence with the rotor passages respectively, and a rotor operating knob with a calibrated dial and a spring-biased positioning detent for engaging the respective pockets, the operating knob also having a locking detent for engaging the cover in the valve off-position, and a separate control button in the knob operable to release the detent.

4. An anesthetic vaporizer as specified in claim 1 wherein the valve seat has a pair of diametrically disposed concentric arcuate slots that are arranged to be in vertical alignment with the arcuate row of rotor passages according to the angular position of the rotor, one of the slots connecting with a port leading to the vaporizer outlet passage and the other slot connecting with a port leading to the vaporizing chamber.

5. An anesthetic vaporizer as specified in claim 1 wherein the rotor passages comprise tubes.

6. An anesthetic vaporizer as specified in claim 5 wherein the passages are of varying diameters.

7. An anesthetic vaporizer as specified in claim 5 wherein the passages are formed by bores through the rotor, and corresponding tubes are fitted in the bores so as to form extensions of the bores respectively.

8. An anesthetic vaporizer for adding the vapor of a volatile liquid anesthetic in predictable increments to a preset flow of gas comprising:
   a. a gas inlet passage and a gas and vapor outlet passage,
   b. a vaporizing chamber containing liquid anesthetic,
   c. a rotary valve assembly for controlling passages connecting the vaporizing chamber to the inlet and outlet passages, and for bypassing the vaporizing chamber comprising a disc-like valve rotor and an enclosing cylinder-like body having a fixed circular seat for the rotor,
   d. the rotor and seat being in planar contact and having in combination a plurality of ports and passageways arranged to form a first proportioning multiple-passage laminar-flow control path from the gas inlet passage through the vaporizing chamber to the outlet passage and a second proportioning multiple-passage laminar-flow control path from the gas inlet through the valve bypassing the vaporizing chamber to the outlet passage,
   e. the valve rotor having a calibrated operating dial and being angularly adjustable to proportion the flow between the first and second paths for adjusting the vapor concentration in the outlet mixture,
   f. a third laminar-flow control path for connecting the gas inlet passage to the outlet passage to bypass the vaporizing chamber, said third path having a single variable restriction for laminar flow control that is defined by nested conical members with restricted spacing for preset minimum laminar flow,
   g. temperature responsive means in the vaporizing chamber for varying the spacing between the conical members to thereby control gas flow in said third path and compensate for variations in the vapor pressure of the liquid anesthetic, and
   h. the valve enclosing body has on its base side a horizontal labyrinth-like groove, and a partition plate between the vaporizing chamber and the valve body covers the groove to form a labyrinthean passage that connects the outlet of the vaporizing chamber with the rotary valve.

9. An anesthetic vaporizer as specified in claim 8 wherein the valve rotor has a central circular recess on its seating face connecting with a valve seat port leading from the labyrinthean vaporizing chamber, and the recess has a radial extension that is arranged to be in registry with a seat passageway leading to the outlet passage.

10. An anesthetic vaporizer as specified in claim 9 wherein the radial extension of the rotor recess connects in the off-position of the valve with a separate valve seat passage leading to atmosphere for separately venting the vaporizing chamber.

11. An anesthetic vaporizer for adding the vapor of a volatile liquid anesthetic in predictable increments to a preset flow of gas comprising:
   a. a gas inlet passage and a gas and vapor outlet passage,
   b. a vaporizing chamber containing liquid anesthetic,
   c. a rotary assembly for controlling passages connecting the vaporizing chamber to the inlet and outlet passages, and for bypassing the vaporizing chamber comprising a disc-like valve rotor and an enclosing cylinder-like body having a fixed circular seat for the rotor,
   d. the rotor and seat being in planar contact and having in combination a plurality of ports and passageways arranged to form a first proportioning multiple-passage laminar-flow control path from the gas inlet passage through the vaporizing chamber to the outlet passage, and a second proportioning multiple-passage laminar-flow control path from the gas inlet through the valve bypassing the vaporizing chamber to the outlet passage,
   e. the valve rotor having a calibrated operating dial and being angularly adjustable to proportion the flow between the first and second paths for adjusting the vapor concentration in the outlet mixture,
   f. a third laminar-flow control path for connecting the gas inlet passage to the outlet passage to bypass the vaporizing chamber, said third path having a single variable restriction for laminar flow control that is defined by nested conical members with restricted spacing for preset minimum laminar flow,
   g. temperature responsive means in the vaporizing chamber for varying the spacing between the conical members to thereby control gas flow in said third path and compensate for variations in the vapor pressure of the liquid anesthetic,
   h. the conical members in the third path constituting a conical valve and seat having a minimum closing clearance and having laminar flow characteristics throughout its variable clearance range, and the valve clearance is controlled by a thermal motor located in the vaporizing chamber at its outlet,
   j. the conical valve being of the double-cone type with the inner cone connected to the thermal motor for varying the valve clearance, and the outer cone constitutes part of a fixed housing mounted within the valve body, j. the thermal motor being of the metallic bellows type that is within and attached to a cylindrical housing that extends in depending relation from the cone valve housing, the depending house being disposed in the vaporizing chamber in the path of exhaust vapor therefrom, and k. the depending motor housing is vertically adjustable with respect to the cone housing for causing adjustment of the minimum valve clearance.

12. An anesthetic vaporizer comprising a housing forming a vaporizing chamber containing liquid anesthetic and a liquid absorbing wick assembly extending into the liquid, a control valve assembly with gas inlet and outlet passages respectively, mounted on the housing to proportion the flow of inlet gas through, respectively, one path including the vaporizing chamber, and another path constituting a bypass passage to the outlet passage, the chamber having inlet and outlet passages extending vertically along opposite sides of the chamber respectively, the wick assembly comprising a stack of alternating planar and corrugated sheets forming a plurality of parallel passages extending horizontally across the chamber throughout its height, the stack substantially filling the chamber, and the horizontal passages connecting at opposite edges of the stack with the chamber inlet and outlet vertical passages respectively, the planar sheets, at each side of a corrugated sheet, are formed by a lamina comprised of a planar sheet of thermally conductive material interposed between planar sheets of absorbent material.

* * * * *

UNITED STATES PATENT AND TRADEMARK OFFICE
CERTIFICATE OF CORRECTION

PATENT NO. : 4,059,657
DATED : November 22, 1977
INVENTOR(S) : WAYNE W. HAY

It is certified that error appears in the above-identified patent and that said Letters Patent are hereby corrected as shown below:

Col. 1, line 59, "aove" should be spelled -- above --.

Col. 2, line 62, "proportional" should be spelled -- proportioned --.

Col. 3, line 12, "ody" should be spelled -- body --.

Col. 3, line 48, "and" after "62" and before "that" should be omitted.

Col. 5, line 15, "stell" should be spelled -- steel --.

Col. 6, line 17, "149" should read -- 148 --.

Col. 6, line 41, "hs" should be spelled -- has --.

Col. 6, line 43, "outlets" should read -- outlet --.

Col. 7, line 17, "accordind" should be spelled -- according --.

Col. 7, line 29, "bory" should be spelled -- body --.

Col. 8, line 19, "leads" should read -- lead --.

Col. 8, line 41, "capillary" after "the" and before "passages" should have been omitted Col. 9, line 3, "by" should read -- the --.

Col. 9, line 10, "FIG." should read -- FIGS. --.

Col. 9, line 44, "acial" should be spelled -- axial --.

Col. 12, line 12, Claim 9, after "labyrinthean" and before "vaporizing" insert -- passage --

UNITED STATES PATENT AND TRADEMARK OFFICE
CERTIFICATE OF CORRECTION

PATENT NO. : 4,059,657
DATED : November 22, 1977
INVENTOR(S) : WAYNE W. HAY

It is certified that error appears in the above-identified patent and that said Letters Patent are hereby corrected as shown below:

Col. 12, line 27, Claim 11c, after "rotary" and before "assembly" insert -- valve --.

Col. 12, line 64, Claim 11i, "j." should read -- i. --.

Col. 13, line 4, Claim 11j, "house" should read -- housing --.

Signed and Sealed this

Fourth Day of April 1978

[SEAL]

Attest:

RUTH C. MASON
Attesting Officer

LUTRELLE F. PARKER
Acting Commissioner of Patents and Trademarks